United States Patent [19]

Steffen

[11] 4,380,632
[45] Apr. 19, 1983

[54] METHOD OF PREPARING QUINOLINES, NAPHTHYRIDINES AND OTHER NITROGEN BI-HETEROCYCLIC COMPOUNDS

[75] Inventor: Klaus-Dieter Steffen, Hennef, Fed. Rep. of Germany

[73] Assignee: Dynamit Nobel Aktiengesellschaft, Troisdorf, Fed. Rep. of Germany

[21] Appl. No.: 286,432

[22] Filed: Jul. 24, 1981

[30] Foreign Application Priority Data

Jul. 28, 1980 [DE] Fed. Rep. of Germany ....... 3028520

[51] Int. Cl.$^3$ ................ C07D 471/00; C07D 487/00; C07D 215/16; C07D 215/20
[52] U.S. Cl. .................................... 544/279; 546/153; 546/156
[58] Field of Search ................ 546/153; 544/279, 153, 544/156

[56] References Cited

U.S. PATENT DOCUMENTS

| | | | |
|---|---|---|---|
| 2,504,874 | 4/1950 | Price et al. | 546/153 |
| 2,504,875 | 4/1950 | Price et al. | 546/153 |
| 3,149,104 | 9/1964 | Lesher et al. | 546/156 |
| 3,673,193 | 6/1972 | Lesher et al. | 546/156 |
| 3,856,800 | 12/1974 | Bair | 546/156 |

OTHER PUBLICATIONS

Surrey, A. R. et al., J. American Chem. Soc., 68, (1946) 113–116.
Lin, A. J. et al., Journal of Medicinal Chem., (1978), vol. 21, No. 3, pp. 268–272.

*Primary Examiner*—Donald G. Daus
*Assistant Examiner*—Sharon A. Gibson
*Attorney, Agent, or Firm*—Sprung, Horn, Kramer & Woods

[57] ABSTRACT

A method for the preparation of nitrogen bi-heterocyclic compounds is disclosed involving the saponification of a compound of the formula

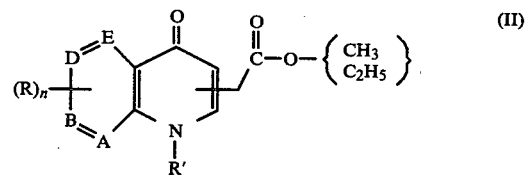

wherein R, E, D, B, A, and R' have the previously assigned significance which comprises saponifying the same by contacting it with at least a stoichiometric amount of water followed by decarboxylation.

The carboxylic acid esters can be those formed by cyclization of dicarboxylic acid esters such as alpha-picolylaminomethylenemalonic acid diethyl ester.

21 Claims, No Drawings

METHOD OF PREPARING QUINOLINES, NAPHTHYRIDINES AND OTHER NITROGEN BI-HETEROCYCLIC COMPOUNDS

BACKGROUND OF THE INVENTION

1. Field of the Invention

The invention relates to a new method of preparing quinolines, naphthyridines and other nitrogen bi-heterocyclic compounds of the general formula

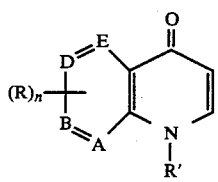

These nitrogen bi-heterocyclic compounds are known from the literature.

2. Discussion of Prior Art

Organ. Synthesis, Vol. III, p. 272 presents a review of a number of syntheses, especially of 4,7-dichlorquinoline. For example, according to J. Amer. Chem. Soc. 68 (1946), 113, 4-hydroxy-7-halogen-quinoline is prepared from the corresponding 2-carbethoxy derivative, and, according to J. Amer. Chem. Soc. 68 (1946), 1204, 4-hydroxy-7-chlorquinoline is prepared from the 3-carbethoxy derivative in two separate stages by alkaline hydrolysis, separation of the solid from the carboxylic acid by filtration, and decarboxylation of the latter in mineral oil. According to J. Med. Chemistry 21 (1978), 268, the production of 6-, 7- or 8-halogen-4-hydroxyquinolines, and, according to J. Heterocycl. Chem. 11 (1974), 849, the production of 4-hydroxyquinolines methoxylated in the 6th position or ethoxylated in the 7th position, is accomplished, again by alkaline saponification and by decarboxylation in high-boiling solvents, after an intervening isolation of the acid. 4-Oxo-6-methyl-6,7,8,9-tetrahydro-homopyrimidazole has also been synthesized by alkaline saponification followed by decarboxylation, according to Arzneimittelforschung 22 (1972), 815. From U.S. Pat. No. 3,856,800 it is apparent that 4-hydroxy-7-methyl-naphthyridine-1,8 can be prepared by means of first stages of an N-oxide from which the oxygen has to be removed again at the end by hydrogenolysis. Boiling 18% hydrochoric acid has been used for the hydrolysis of 3-carbethoxy-4-hydroxy-6-methoxyquinoline according to J. Amer. Chem. Soc. 68 (1946), 1204, and of 5-hydroxy-6-carbethoxy-naphthyridine-1,7 according to Liebigs Ann. Chemie 4 (1979), 443. In the case of the latter compound, decarboxylation to 5-hydroxy-naphthyridine-1,7 occurred, which then had to be purified by sublimation.

These known methods of preparation have in common the necessity to use at least a stoichiometric amount of alkali or hydrochloric acid, which then has to be neutralized, resulting in large amounts of salt solutions, which today create disposal problems.

It is furthermore disadvantageous that these syntheses are two-step syntheses on account of the isolation and washing of the acid prior to the decarboxylation, resulting in high costs when the method is applied on a large production scale.

It, therefore, became desirable to provide a method which produces little waste, is easy to perform, and nevertheless gives good yields and purities in the final products. The solution of this problem is described hereinbelow.

SUMMARY OF THE INVENTION

The starting substance (general formula II below) is prepared in a few minutes by the cyclization of compound III at high temperatures of about 240°–350° C. with the splitting off of ethanol or methanol:

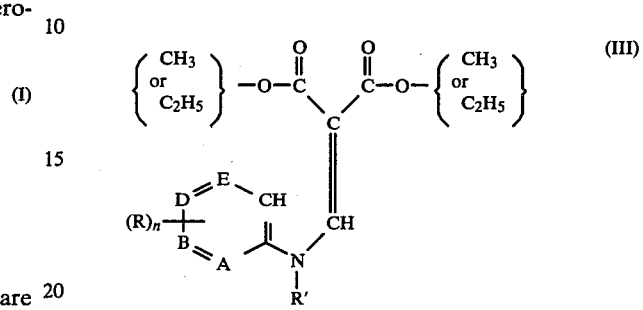

The solvents used are high-boiling substances such as diphenylether, dibenzylbenzene, benzylbenzene, diethylphthalate, polyphosphoric acid, silicone oil, triphenylmethane or a wide variety of commercially available paraffin oils and heat transfer oils, such as for example those described in German Offenlegungsschrift Nos. 2,343,462 and 2,441,747 and in U.S. Pat. Nos. 3,149,104 and 3,673,193.

The subject matter of the invention is a method of preparing quinolines, naphthyridines and other nitrogen biheterocyclic compounds of the general formula (I)

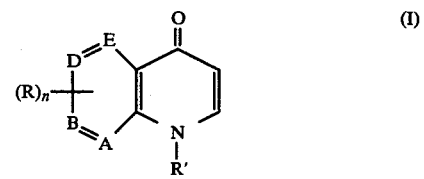

wherein R can be H, halogen, nitro, amino, keto, alkyl, alkenyl, aryl (substituted aryl), or haloalkyl groups, or aryl or alkyl substituents bound by N, O, S or $SO_2$, in linear or cyclic arrangement, R' represents H, aryl, alkyl, alkenyl, or haloalkyl substituents, the letters A, B, D and E represent carbon atoms or as many as 3 can represent nitrogen atoms, the rest carbon atoms, and n represents an integer from 0 to 4, which is characterized by the fact that the corresponding carbethoxy or carbomethoxy compounds of the general formula II obtained in suspension from the cyclization reaction:

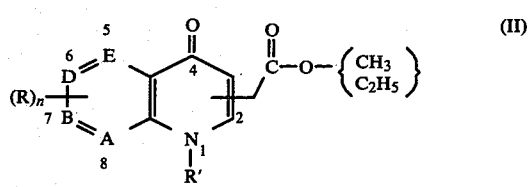

are, without any intervening isolation, first saponified with water, under pressure, in the presence of acid catalysts, and then decarboxylated to compound I which can be isolated at this time if desired or, if not, the saponification is directly succeeded by other reactions.

In the saponification of the esters to the carboxylic acids, water is to be added in at least a stoichiometric amount. The ester is suspended or dissolved in one of the above-mentioned high-boiling liquids.

Without intervening isolation, the compound II from the cyclization is treated in an autoclave with water in a volumetric ratio of 1:0.5 to 1:5 ($H_2O$:suspension), preferably of 1:1.0 to 1:3.0. 0.05 to 3.0, preferably 0.3 to 0.6%, by weight, of an acid catalyst such as sulfuric acid, p-toluenesulfonic acid, phosphoric acid or hydrochloric acid, is dissolved in the water. Acid ion exchangers are also usable if they have sufficient thermal stability. The saponification is performed with gradual removal of alcohol by distillation, at 120 to 250, preferably 150° to 180° C., at 4 to 8 bar, within 4 to 8 h. The reaction is ended when nothing but water is being distilled out. At that time the mixture is cooled to about 80° to 95° C., the amount of aqueous concentrated alkali lye necessary for the neutralization of the acid catalyst, especially caustic soda solution or caustic potash solution, is added, and all of the water is distilled out at gradually rising temperatures. No isolation of the carboxylic acid is performed at this point, either. After a bottom temperature of approximately 190° to 210° C. is reached, the decarboxylation begins, that is, carbon dioxide is released. The temperature is further increased to 230° to 240° C., and the reaction mixture is let stand at this teperature for 3 to 8 hours as a rule, until the end of the reaction is determined by the fact that the formation of carbon dioxide has ended. Decarboxylation is carried out at a pressure of 30 Torr to 2 atmospheres absolute.

The concentration of the suspension of compound II in the high-boiling liquid, which can vary between 2% and 15% by weight, the concentration of the catalyst, and the reaction time as well as the reaction temperatures are factors which influence one another. A higher concentration of compound II requires higher catalyst concentrations or intensified reaction conditions, i.e., higher temperature and, if necessary, longer time of reaction.

To improve the wetting of the high-boiling liquid with water, it is recommendable to add one or more drops of a commercial wetting agent or surfactant. It can also be advantageous to add to the water phase transfer catalysts, such as benzyltriethyl ammonium chloride, benzyl trimethyl ammonium chloride, tetramethyl ammonium chloride, or benzyltriphenylphosphonium chloride.

It is also to be recommended that the catalyst acid be neutralized after saponification has been completed, since otherwise the decarboxylated end product will be darkened.

After this multi-step one-pot reaction, when the end product is in the heat transfer agent, another reaction can follow directly, such as for example the chlorination of HCC with phosphorus oxychloride, as described in Org. Synth. Vol. III, p. 272, and only after that is the end product to be worked up in the manner described therein. If necessary, the isolation of compound I is to follow the decarboxylation.

Since the high-boiling liquids can be removed only very poorly by drying, a washing must be performed with more readily volatile solvents. Examples of such solvents are the aliphatic and aromatic hydrocarbons, such as the hydrocarbons of 5 to 10 carbon atoms, toluene, xylenes, petroleum ethers, alcohols such as methanol, ethanol, methoxyethanol, propanol and butanol, and ketones such as acetone and butanone. For the complete removal of the catalyst salts, it is recommendable to wash with water, especially in the case of weak, non-polar solvents. To the extent that compound I is pooly soluble in these solvents, they can also be used as agents for precipitating compound I out of the high-boiling liquid and thus they can be used in a volumetric ratio of suspension to liquid of 1:0.1 to 1:10. This increases the yield of compound I, but usually to the detriment of purity.

In accordance with the invention, it has been found to be especially advantageous to crystallize compound I by cooling, filtering and washing with acetone until all of the high-boiling liquids have been removed, and then washing with a small amount of water. This results in good yields of 75 to 90% of the theory, as well as good purities of up to 90% and more. This method of processing can be very important whenever position-isometric compounds of the same molecular weight in small concentrations are undesirable in subsequent reactions or in the use to which the product is to be put, an example being 4-hydroxy-5-chloroquinoline in 4-hydroxy-7-chlorquinoline.

The solvents used, such as the high-boiling liquids which are used in the reactions, or the low-boiling liquids that are used for the washing of compound I, can be distilled after one or more uses, and reused. The bottom products of the distillation, which are produced at a very low rate, can be disposed of by burning.

The problem set forth above is therefore solved. Only small amounts of by-products and salts are formed and are easy to remove. Surprisingly, only a catalytically effective amount of acid is necessary for the saponification, and the reaction can be performed in one step without isolation of the intermediate products.

The amazingly high yields and purities of this multiple-step, single-pot process far exceed the total yield of compound I with respect to compound II from the known multiple-step process.

The products of the process are important intermediates in the synthesis of drugs. Known products such as chloroquine, glafenin or nalidixic acid can be prepared from them.

EXAMPLES

Abbreviations used:
CHCC: 3-carbethoxy-4-hydroxy-7-(or 5-)chlorquinoline
HCC: 4-hydroxy-7-(or 5-)chlorquinoline
PMME: α-picolylaminomethylenemalonic acid diethyl ester
CHMN: 3-carbethoxy-4-hydroxy-7-methyl-naphthyridine-1,8
HMN: 4-hydroxy-7-methyl-naphthyridine-1,8
p-TSS: p-toluenesulfonic acid.

EXAMPLES 1 TO 4

A 5 wt.-% suspension of CHCC in benzylbenzene was placed in a steel autoclave equipped with stirrer, temperature indicator, pressure gauge and pressure maintaining valve, with a condenser attached, and an equal volume of water was added in which the acid catalysts listed in the following table were dissolved in various concentration, plus a few drops of surfactant. After the autoclave was closed, it was heated for 8 hours at 150° C., and ethanol and water were gradually distilled out. Then the contents were cooled overnight, neutralized with the amount of 10 wt.-% NaOH equivalent to the catalyst acid, and then reheated without pressure with distillation of the remaining water. The internal temperature was maintained for 4 hours at 230° to 240° C., until the formation of $CO_2$ had ended. The autoclave contents were cooled, diluted with twice the volume of heptane, and the HCC was filtered out, washed with heptane, and dried. The yield relates to the m-chloraniline put in; the purity is stated in surface-percent, determined by HPLC, i.e., high-pressure liquid chromatography.

| Example No. | Catalyst Kind | % sol. in H₂O | HCC yield [% of th.] | Purity [HPLC surface %] | | |
|---|---|---|---|---|---|---|
| | | | | unreacted | HCC-7 | HCC-5 |
| 1 | H₃PO₄ | 0.25 | 90.7 | 1.5 | 96.7 | 1.8 |
| 2 | H₃PO₄ | 0.50 | 90.1 | 0 | 97.8 | 2.3 |
| 3 | H₂SO₄ | 0.25 | 85.8 | 0.3 | 95.1 | 1.8 |
| 4 | p-toluenesulfonic acid | 0.125 | 85.6 | 0 | 98.0 | 1.0 |

EXAMPLES 5 TO 7

As in Examples 1 to 4, a 5 wt.-% suspension of CHCC in benzylbenzene was diluted in a pressure autoclave with only one third of its volume of water containing the varying amounts of p-toluenesulfonic acid listed in the following table, plus a few drops of wetting agent. The mixture was heated for 8 hours at 150° C. with removal of ethanol and $H_2O$ by distillation; and the p-toluenesulfonic acid was neutralized with NaOH, and the mixture was heated without pressure at 230° to 240° C. until, after four hours, the formation of $CO_2$ had ended. After cooling, the reaction mixture was diluted with twice its volume of heptane, and the HCC was filtered out, washed with heptane and dried.

| Example No. | p-TSS concentration [% in H₂O] | HCC yield [% of the theory] | Purity [HPLC surface %] | | |
|---|---|---|---|---|---|
| | | | Unreacted | HCC-7 | HCC-5 |
| 5 | 0.5 | 83.4 | 0.6 | 97.6 | 1.2 |
| 6 | 0.25 | 85.6 | 3.3 | 94.2 | 2.3 |
| 7 | 0.125 | 87.1 | 19.0 | 78.7 | 2.1 |

EXAMPLES 8 AND 9

As in Examples 1 and 4, a 5 wt.-% suspension of CHCC in benzylbenzene was prepared and treated in a VA steel autoclave with only half the amount of water containing in solution 0.5 wt.-% and 0.25 wt.-% of p-toluenesulfonic acid plus 1 drop of wetting agent. For the saponification, the mixture was heated at 160° C. under pressure for 8 and 4 hours, with distillation of ethanol and $H_2O$. After the p-toluenesulfonic acid had been neutralized with 20 wt.-% caustic KOH, it was heated for 5 hours at 230° to 240° C., cooled, and diluted with heptane, and the HCC was filtered out, washed, and dried.

| Example No. | p-TSS concentration [% in H₂O] | Saponification time [h] at 160° C. | HCC yield [% of the theory] | Purity [HPLC surface %] | | |
|---|---|---|---|---|---|---|
| | | | | Unreacted | HCC-7 | HCC-5 |
| 8 | 0.5 | 8 | 89.3 | 0 | 98.4 | 1.6 |
| 9 | 0.25 | 4 | 91.8 | 1.1 | 97.0 | 1.8 |

EXAMPLES 10 TO 12

Washed and dried CHCC was again suspended in dibenzylbenzene in amounts of 4, 6 and 8 weight-percent, and treated in an autoclave with half the volume of water in which 0.5 wt.-% of p-toluenesulfonic acid and 1 drop of wetting agent were dissolved. After saponification at 160° C. within 5 hours, the mixture was cooled, the p-toluenesulfonic acid was neutralized, and the decarboxylation was performed within 5 hours at 230° C. The results are recorded in the following table:

| Example No. | CHCC concentration [%] | HCC Yield [% of the theory] | Purities [HPLC surface %] | | |
|---|---|---|---|---|---|
| | | | unreacted | HCC-7 | HCC-5 |
| 10 | 4 | 81.4 | 1.1 | 97.5 | 0.9 |
| 11 | 6 | 88.0 | 13.6 | 85.3 | 0.9 |
| 12 | 8 | 86.6 | 16.6 | 82.5 | 0.8 |

EXAMPLES 13 TO 15

In these examples the cyclization reaction was performed in accordance with German Offenlegungsschrift No. 2,343,462 such that a 9, 6 or 4% suspension of CHCC in benzylbenzene resulted at the end. Each of the two suspensions was treated in the autoclave with half its volume of water in which 0.3 to 0.4 wt.-% of p-toluenesulfonic acid and one drop of wetting agent were dissolved. For the saponification, the mixture was heated for 6 hours at 170° C. with distillation of ethanol and $H_2O$, and then the p-toluenesulfonic acid was neutralized and the decarboxylation was performed in 6 hours at 240° C. The HCC was separated by crystallization overnight, filtered, then washed thrice with a little acetone and twice with water, and dried. The yields and purities are given in the following table.

| Example No. | CHCC concentration [%] | HCC yield [% of the theory] | Purities [HPLC surf. %] | | |
|---|---|---|---|---|---|
| | | | Unreacted | HCC-7 | HCC-5 |
| 13 | 9 | 75.1 | traces | 99.5 | 0.2 |
| 14 | 6 | 76.2 | " | 99.7 | 0.1 |
| 15 | 4 | 77.7 | " | 99.2 | 0.3 |

EXAMPLE 16

First a cyclization reaction to CHCC was performed, so that at the end a 9 wt.-% suspension in benzylbenzene resulted. After transfer to an autoclave, the suspension was mixed with half its volume of water in which 0.4 wt.-% of p-toluenesulfonic acid and a few drops of wetting agent were dissolved. Saponification was completed in 6 hours at 160° C. with distillation of ethanol and $H_2O$, the catalyst was neutralized, and then the mixture was decarboxylated within six hours at 230° C. After cooling, the reaction mixture was treated with 2.5 times its volume of heptane and the precipitated HCC was filtered out, washed with a little heptane and acetone, and dried.

Yield: 85.0% of the theory; Purity: 95.5% HCC-7, 0.8% HCC-5, 3.5% by-products.

EXAMPLE 17

60 g of PMME was cyclized in 1.05 liter of dibenzylbenzene, so that a 4.0 wt.-% suspension of CHMN resulted. This was transferred to an autoclave and 550 ml of water in which 0.5 wt.-% of p-toluenesulfonic acid was dissolved was added and mixed; one drop of wetting agent was added, and the mixture was saponified under pressure at 170° C. within 8 hours with distillation of ethanol and H$_2$O. After the neutralization of the catalyst acid, the mixture was decarboxylated to HMN without pressure, at 240° C., within approximately 5 hours. The mixture was cooled overnight and filtered; the product was washed first with heptane and then with a mixture of acetone and water, and dried.

Yield: 19.7 g (86% of the theory) M.P.: 232°–234° C. (a resublimated sample had a melting point of 236° C.).

Purity (HPLC surface %): 97.5% HMN, 1.3% CHMN, 1.2% other by-products.

EXAMPLE 18

A 4% suspension of 2-chloro-5-oxo-6-carbethoxy-5,8-dihydropyrido[2,3d]-pyrimidine in dibenzylbenzene is saponified under pressure in the above-described manner and, after distillation of the excess water, the reaction mixture is decarboxylated to 2-chloro-5-oxo-5,8-dihydro-pyrido[2,3d]-pyrimidine

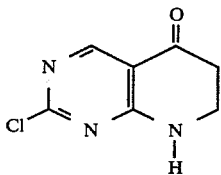

This chloropyridopyrimidine can be isolated as such, or the chloro group can be made to react directly with amines such as dialkylamines, pyrrolidine, or N-monosubstituted piperazines, after the addition of a base to intercept HCl, or with alkali salts of organic acids, or with alkali alcoholates as well as alkali thioalcoholates, and only then isolated.

What is claimed is:

1. A method for preparing a nitrogen heterocyclic of the formula

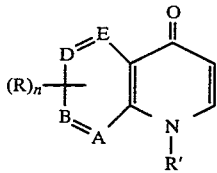

wherein
R=hydrogen, halogen, nitro, amino, keto, alkyl, alkenyl, substituted aryl, unsubstituted aryl, haloalkyl or aryl or alkyl substituents having a nitrogen, oxygen sulfur or SO$_2$ moiety in the chain or in a cyclic arrangement;
R'=hydrogen, aryl, alkyl, alkenyl or haloalkyl; A, B, D, E, represent nitrogen or carbon atoms with up to 3 of said A, B, and D, representing nitrogen and the balance representing carbon atoms;
n is an integer from 0 to 4 which comprises saponifying a compound of the formula

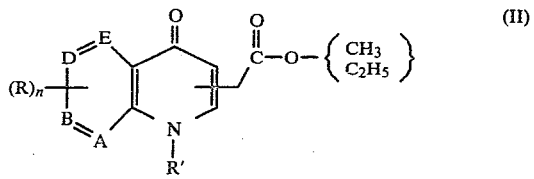

wherein
R, E, D, B, A, and R' have the previously assigned significance by contacting the same with at least a stoichiometric amount of water in the presence of an acid catalyst in an amount of 0.05 to 3 weight percent under a pressure of 4 to 8 bars distilling out the alkanol, neutralizing the acid, and thereafter decarboxylating the so-saponified compound without isolating the product of saponification.

2. A process according to claim 1, wherein the saponification is performed in water employing a volumetric ratio of water to the compound to be saponified in a high-boiling liquid of 1:0.5 to 1:5 and the saponification is effected at a temperature of 120° to 250° C.

3. A process according to claim 2, wherein alcohol is simultaneously distilled over during the saponification.

4. A process according to claim 3, wherein the volumetric ratio of water to compound to be saponified is in the range of 1:1 to 1:3.

5. A process according to claim 3, wherein the saponification is effected at a temperature of 150° to 180° C.

6. The process according to claim 1, wherein the acid catalyst is present in an amount of 0.3 to 0.6 weight percent.

7. A process according to claim 2, wherein the acid catalyst is sulfuric acid, p-toluene sulfonic acid, phosphoric acid, hydrochloric acid, or an acid ion exchanger.

8. A process according to claim 1, wherein the acid catalyst is neutralized with an alkali after saponification has ended and the water present is distilled out.

9. A process according to claim 8, wherein neutralization of the acid is effected prior to decarboxylation.

10. A process according to claim 1, wherein decarboxylation is performed by heating the so-saponified compound at a temperature of 190° to 240° C.

11. A process according to claim 10, wherein decarboxylation is effected at a temperature of 230° to 240° C.

12. A process according to claim 10, wherein decarboxylation is effected by heating the so-saponified compound for a period of 3 to 8 hours.

13. A process according to claim 1, wherein following saponification and decarboxylation, the end product is washed with a solvent.

14. A process according to claim 13, wherein said solvent is a hydrocarbon alcohol, ketone or water, or a mixture thereof.

15. A process according to claim 1, wherein the compound to be saponified is one which has been prepared by cyclizing a compound of the formula

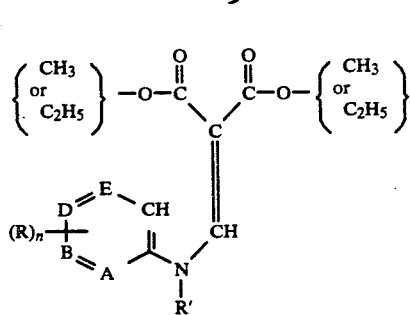 (III)

wherein A, B, D, E, R, R' and n have the previously assigned significance.

16. A process according to claim 15, wherein cyclization of said compound is effected by heating the same at a temperature of about 240° to 350° C. and removing methanol or ethanol.

17. A process according to claim 16, wherein cyclization is performed in the presence of an inert high boiling liquid which is not boiled off when the cyclization is effected.

18. A process according to claim 16, wherein the resultant ester of the cyclization is thereafter saponified without intervening isolation thereof.

19. A process according to claim 1, wherein 3-carbethoxy-4-hydroxy-(5 or 7) chlorquinoline is saponified and thereafter decarboxylated.

20. A process according to claim 1, wherein 2-chloro-5-oxo-6-carbethoxy-5,8 dihydropyrido[2,3d]pyrimidine is saponified and the resultant acid is thereafter decarboxylated.

21. A process according to claim 15, wherein alphapicolylaminomethylenemalonic acid diethyl ester is cyclized to form 3-carbethoxy-4-hydroxy-7-methyl-naphthyridine-1,8 and said naphthyridine is saponified and decarboxylated whereby to form 4-hydroxy-7-methyl-naphthyridine-1,8.

* * * * *